United States Patent [19]

Soni et al.

[11] Patent Number: 5,955,350

[45] Date of Patent: *Sep. 21, 1999

[54] SEQUENTIAL BIOLOGICAL/CHEMICAL/ BIOLOGICAL TREATMENT OF ORGANIC WASTE

[75] Inventors: Bhupendra K. Soni, Westmont; Kevin Kayser, Chicago; Robert L. Kelley, Arlington Heights; Vipul J. Srivastava, Woodridge, all of Ill.

[73] Assignee: Institute of Gas Technology, Des Plaines, Ill.

[ * ] Notice: This patent is subject to a terminal disclaimer.

[21] Appl. No.: 08/800,134

[22] Filed: Feb. 13, 1997

Related U.S. Application Data

[63] Continuation-in-part of application No. 08/402,421, Mar. 10, 1995, Pat. No. 5,610,065, which is a continuation-in-part of application No. 08/056,527, May 3, 1993, abandoned, which is a continuation-in-part of application No. 07/718,330, Jun. 21, 1991, abandoned.

[51] Int. Cl.$^6$ .................................................. D06M 16/00
[52] U.S. Cl. ..................... 435/264; 435/262.5; 588/205; 588/207; 588/218
[58] Field of Search ................................ 435/262, 262.5, 435/264; 588/248, 205, 206, 207, 218

[56] References Cited

U.S. PATENT DOCUMENTS

| | | |
|---|---|---|
| 4,234,689 | 11/1980 | Gutnick et al. . |
| 4,321,143 | 3/1982 | Wilms et al. . |
| 4,370,241 | 1/1983 | Junkermann et al. . |
| 4,387,018 | 6/1983 | Cook et al. . |
| 4,447,541 | 5/1984 | Peterson .................................. 435/264 |
| 4,604,214 | 8/1986 | Carr et al. . |
| 4,724,084 | 2/1988 | Pahmeier et al. . |
| 4,804,480 | 2/1989 | Jayawant . |
| 4,954,258 | 9/1990 | Little ........................................ 435/264 |
| 5,334,533 | 8/1994 | Culasito et al. .......................... 435/264 |
| 5,610,065 | 3/1997 | Kelley et al. ............................. 435/264 |

FOREIGN PATENT DOCUMENTS

| | | | |
|---|---|---|---|
| 2171382 | 9/1996 | Canada ............................. A62D 3/00 |
| 2533775 | 3/1997 | Germany . |

OTHER PUBLICATIONS

Sang H. Lee and Judith B. Carberry: Biodegradation of PCP enhanced by chemical oxidation pretreatment, *Water Environment Research*, vol. 64, No. 5, Alexandria, Virginia, pp. 682–690, 1992.

Joachim Behrendt: Biologisch–chemische Behandlung eines kontaminierten Grundwassers von einem Gaswerksgelände, *GWf: Das Gas–und Wasserfach*, vol. 136, No. 1, Munchen, Germany pp. 18–24, 1995.

Mueller J.G. et al., "Isolation and Characterization of a Fluoranthene–Utilizing Strain of *Pseudomonas paucomibilis*" Applied Environmental Microbiology, 56:1079–1086 (1990).

Mueller J.G. et al., Action of Fluoranthene–Ulitizing Bacterial Community of Polycyclic Aromatic Hydrocarbon Components of Creosote, Applied Environmental Microbiology, 55:3085–3090 (1989).

"Catalogue of Bacteria and Phages", American Type Culture Collection, 17th Edition, 1989.

Vipul J. Srivastava, John J. Kilbane, Robert L. Kelley, Cavit Akin, Thomas D. Hayes, and David G. Linz, "Biodegradation of Old Town Gas Site Wastes," IGT Symposium on Gas, Oil, and Coal Biotechnology, New Orleans, Louisiana, Dec. 5–7, 1988.

W. Kennedy Gauger and Vipul J. Srivastava, "Bioremediation of Gas Industry Wastes: Current Status and New Directions," Hazardous Waste and Environmental. Management in the Gas Industry Symposium, Chicago, Illinois, Jun. 13, 1990.

Bedard, D. L. et al., *Applied and Environmental Microbiology*, 51(4), pp. 761–768, Apr. 1986.

*Primary Examiner*—David A. Redding
*Attorney, Agent, or Firm*—Pauley Petersen Kinne & Fejer

[57] ABSTRACT

A process for remediation of contaminated solid materials comprising polynuclear aromatic hydrocarbon contaminated solid materials, polychlorinated hydrocarbon contaminated materials, and mixtures thereof by sequential biological/ chemical/biological treatment in which the contaminated solid materials are biodigested under suitable conditions by a first aerobic or anaerobic digestion, producing a first biodigestion product. The first biodigestion product is then contacted for chemical treatment with hydrogen peroxide in the presence of ferrous ion in amounts and under conditions suitable for chemical oxidation, forming a mixture and oxidizing the first biodigestion product, producing biodegradable hydrocarbon product materials having enhanced biodegradability. The product materials are then biodigested under suitable conditions by a second aerobic or anaerobic digestion.

20 Claims, 16 Drawing Sheets

SEQUENTIAL BIOLOGICAL/CHEMICAL/ BIOLOGICAL TREATMENT OF ORGANIC WASTE

CROSS REFERENCE TO RELATED APPLICATIONS

This application is a continuation-in-part application of our application having Ser. No. 08/402,421, filed Mar. 10, 1995, now U.S. Pat. No. 5,610,065 which application is a continuation-in-part application of our previously filed application having Ser. No. 08/056,527, filed May 3, 1993, now abandoned, which application is a continuation-in-part application of our previously filed application having Ser. No. 07/718,330, filed Jun. 21, 1991, now abandoned.

BACKGROUND OF THE INVENTION

1. Field of the Invention

This invention relates to sequential biological/chemical/ biological treatment providing improved remediation of undesired organic solid components in materials such as soils, sediments, sludges and slurries containing such solid organopollutants, particularly polynuclear aromatic hydrocarbons (PAH's) and polychlorinated hydrocarbons (PCBs). The process generally involves biological treatment of contaminated solid materials under aerobic conditions followed by chemical oxidation or partial oxidation with hydrogen peroxide in the presence of ferrous ion, such as Fenton's Reagent ($H_2O_2/Fe^{++}$), under specified conditions followed by aerobic microbial digestion.

2. Description of Prior Art

A number of prior art references teach treatment of organic-containing effluents with hydrogen peroxide and iron. U.S. Pat. No. 4,321,143 teaches decreasing COD-content of effluent by treating with hydrogen peroxide in the presence of a transition metal compound, for decomposition of the hydrogen peroxide, by adjusting the pH of the effluent to about 4 to 5, adding about 55 to 63% of the calculated quantity of $H_2O_2$ required for the total oxidation of the total COD-content, dissolving an iron compound in the effluent so that the molar ratio of $H_2O_2$ to iron is about 20:1 to 10:1, maintaining the temperature at about 5° to about 100° C., adding a base to adjust the pH to about neutral, separating flocculated material, and subjecting the effluent to biological degradation.

Oxidation of certain aromatic chemicals using Fenton's Reagent is known: U.S. Pat. No. 4,604,214 teaches removal of nitrocresols from dinitrotoluene waste water streams by adjustment of pH to below about 4 with an aqueous acid followed by contact with Fenton's Reagent, about 1.1 to 3.0 weight ratio of peroxide to total nitrocresols and ferrous salt to provide $2.5–5\times10^{-3}$M, at 70° to 90° C. for about one half to one hour; U.S. Pat. No. 4,804,480 teaches destroying polynitrophenols or their salts in an aqueous waste by treating with at least two moles of hydrogen peroxide per mole of nitrophenol in the presence of from 0.002 to 0.7 moles of an iron salt per mole of polynitrophenol and at a pH lower than 4 and a temperature greater than 65° C.; U.S. Pat. No. 4,370,241 teaches treatment of waste water containing phenol or a phenol derivative with hydrogen peroxide in the presence of metallic iron or copper with a specified activator which is a salt of an alkali metal, alkaline earth metal, zinc, aluminum, nickel, manganese or insoluble silica, the activator being present in an amount of 0.1 to 0.2 percent based upon the hydrogen peroxide, and the treatment is said to be independent of pH.

U.S. Pat. No. 4,724,084 teaches removal of toxic organics and heavy metals from waste water discharged from airplane manufacturing processes by using ferrous sulfate catalyzed hydrogen peroxide at an initial pH of about 5 for oxidation of phenol followed by flocculation of metals and repeating the oxidation step with ferrous sulfate catalyzed hydrogen peroxide.

Soil decontamination by desorption and dehalogenation of polyhalogenated contaminants is taught by U.S. Pat. No. 4,447,541 to be effected by an alkaline constituent of an alkali metal hydroxide and a monohydric or dihydric alcohol together with a sulfoxide catalyst followed by biological degradation of the more highly biodegradable hydrolyzed organics. U.S. Pat. No. 4,387,018 teaches removal of polychlorinated biphenyl from oil by extracting the biphenyls into methanol and separation by distillation.

The publication "Biodegradation of Old Town Gas Site Wastes," Vipul J. Srivastava, John J. Kilbane, Robert L. Kelley, Cavit Akin, Thomas D. Hayes and David G. Linz, *IGT Symposium on Gas, Oil, and Coal Biotechnology*, New Orleans, La., Dec. 5–7, 1988 generally suggests treatment of pyrene and thianthrene with hydrogen peroxide and ferrous sulfate for oxidizing polynuclear aromatic hydrocarbons to complement in-situ biological treatment processes.

A recent review of bioremediation of liquid and solid organic contaminated wastes which points out many problems, particularly in the bioremediation of solids contaminated with aromatic hydrocarbons, most particularly the polynuclear aromatic hydrocarbon contaminants having about 4 to about 6 rings, is provided in "Bioremediation of Gas Industry Wastes: Current Status and New Directions," W. Kennedy Gauger and Vipul J. Srivastava, *Hazardous Waste and Environmental Management in the Gas Industry Symposium*, Chicago, Ill. Jun. 13, 1990.

SUMMARY OF THE INVENTION

It is an object of this invention to provide a process for effective degradation of polychlorinated hydrocarbon materials (PCBs) and polynuclear aromatic hydrocarbon materials (PAHs) in contaminated soils which can reduce the level of said polychlorinated hydrocarbon materials and polynuclear aromatic hydrocarbon materials by greater than 90%.

It is an object of this invention to provide a process for biological degradation followed by high degree chemical oxidation of polynuclear aromatic hydrocarbons and/or polychlorinated hydrocarbons using hydrogen peroxide in the presence of ferrous ion followed by biological degradation to obtain high remediation of polynuclear aromatic hydrocarbon and/or polychlorinated hydrocarbon contaminated solids.

It is another object of this invention to provide an integrated biological/chemical/biological treatment process for remediation of higher polynuclear aromatic hydrocarbon and/or polychlorinated hydrocarbon contaminated solid waste materials in which high concentrations of solids can be treated at about ambient temperatures.

It is yet another object of this invention to provide an integrated biological/chemical/biological treatment process for polynuclear aromatic hydrocarbon and/or polychlorinated hydrocarbon contaminated solid waste materials which is enhanced by the presence of methanol and/or ethanol during chemical treatment with hydrogen peroxide in the presence of ferrous ion.

These and other objects of this invention are achieved by a sequential biological/chemical/biological treatment process for remediation of contaminated solid materials comprising polynuclear aromatic hydrocarbon contaminated solid materials and/or polychlorinated hydrocarbon contaminated materials in which the contaminated solid materials are first biodegraded under suitable conditions by a first aerobic or anaerobic digestion, producing a first biodigestion product. The product of this first aerobic or anaerobic digestion is then contacted for chemical treatment with hydrogen peroxide in the presence of ferrous ion, preferably in a liquid solution, forming a mixture, or slurry, at a temperature of about 20° to about 40° C., oxidizing the polynuclear aromatic hydrocarbons and/or polychlorinated hydrocarbons, thus producing more readily biodegradable hydrocarbon product materials. These more readily biodegradable hydrocarbon product materials are then biodegraded by a second aerobic or anaerobic digestion. The process may be even further enhanced by increased total oxidation of the polynuclear aromatic hydrocarbons and/or polychlorinated hydrocarbons to carbon dioxide in the chemical treatment step by the presence of a lower alcohol in the hydrogen peroxide-containing slurry. The process of this invention is extremely flexible, providing combinations of biological treatments and various manners of recycle. The integrated biological/chemical/biological treatment process according to this invention may also be performed on solids in-situ, such as in-situ contaminated soils.

This process is very effective in degrading PCB congeners. The preferred microorganisms for use in the biodigestion steps are *Alcaligenes eutrophus* and Pseudomonas sp. Surprisingly, we have found that the biological treatment steps work best at a pH in the range of about 4.0 to 6.0, preferably at a pH of 5.0. This is particularly surprising in view of the fact that most of the research to date on *Alcaligenes eutrophus* and Pseudomonas sp. has demonstrated that a pH of 7.5 is optimal for maximum degradation of PCB congeners (Bedard et al., "Rapid Assay for Screening and Characterizing Microorganisms for the Ability to Degrade Polychlorinated Biphenyls," *Applied and Environmental Microbiology*, Apr. 1986, pp. 761–768). A pH in the range of about 4.0 to 6.0 is also beneficial for the chemical treatment step. Operation of the process of this invention under these conditions has led to a degradation of greater than 99% of the PCBs in a PCB-contaminated solid material.

It is known that hydroxylation of organic compounds is a necessary step for biological degradation and increases the solubility of polynuclear aromatic hydrocarbons. It is also known that Fenton's reaction hydroxylates organic compounds. As a result, it is apparent that chemical treatment of the polynuclear aromatic hydrocarbons and polychlorinated hydrocarbons in accordance with the integrated process of this invention increases the biodegradability and bioavailability of the polynuclear aromatic hydrocarbons and the polychlorinated hydrocarbons. By preceding the chemical treatment step with an aerobic digestion step in accordance with the process of this invention, we are able to enhance the efficiency of the chemical process, which, in turn, further enhances the effectiveness of the aerobic digestion step following the chemical treatment step.

Experiments which we have conducted show that more polar intermediates are also formed in the chemical treatment step to provide enhanced biodegradability. In addition, the chemical treatment in accordance with the process of this invention modifies the texture of the soil in which the polynuclear aromatic hydrocarbons and polychlorinated hydrocarbons are disposed as well as the interaction between the sorbed organopollutant and the soil matrix, making the organopollutant more available for desorption and biodegradation. Although biosurfactants are known to be effective on lower molecular weight organic compounds, they have not been shown to be effective on higher molecular weight compounds, such as 4- to 6-ring polynuclear aromatic hydrocarbons. Mueller J. G. et al., "Isolation and Characterization of a Fluoranthane-Utilizing Strain of *Pseudomonas paucimobilis*," *Applied Environmental Microbiology*, 56:1079–1086 (1990) and Mueller, J. G. et al., "Action of Fluoranthene-Utilizing Bacterial Community on Polycyclic Aromatic Hydrocarbon Components of Creosote," *Applied Environmental Microbiology*, 55:3085–3090 (1989) describe the enhanced biodegradability of fluoranthene and other polynuclear aromatic hydrocarbons by the addition of 200 ppm Tween 80, a known surfactant, albeit not a biosurfactant.

It will also be apparent to those skilled in the art that the non-specific nature of the Fenton's reaction requires enough hydrogen peroxide to degrade all organics. In direct contrast thereto, we have found that the polynuclear aromatic hydrocarbons and polychlorinated hydrocarbons sorbed to the soil matrices are selectively degraded and that, as a result, good results are obtained using less hydrogen peroxide.

BRIEF DESCRIPTION OF THE DRAWINGS

The invention will be more fully understood by description of preferred embodiments in conjunction with the drawings wherein.

DESCRIPTION OF PREFERRED EMBODIMENTS

Figure 1:
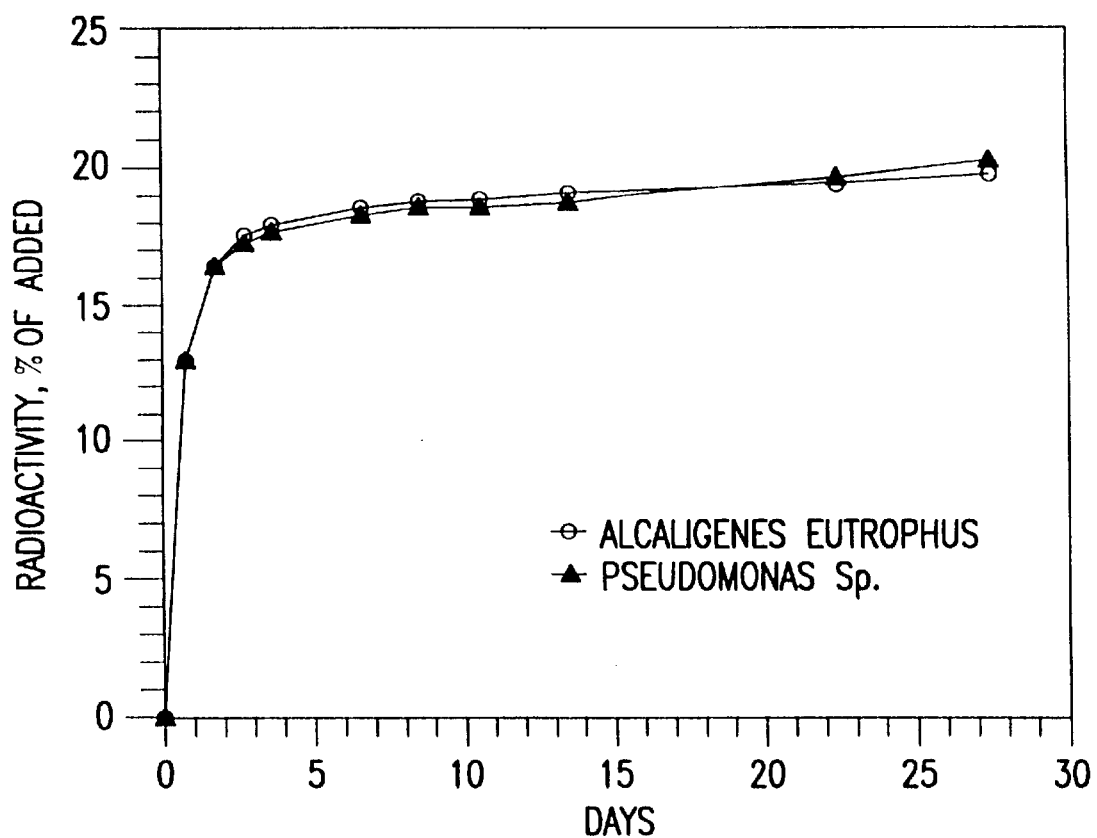
FIG. 1 is a diagram showing the relative effectiveness of the microorganisms utilized in the process of this invention for mineralization of 2-chlorobiphenyl.

As used throughout the specification and claims, the term "mineralization" is defined as meaning the substantially complete degradation of PCBs and PAHs to $CO_2$. "Degradation" is distinguished from "mineralization" in that degradation involves the transformation of PCBs and PAHs to an environmentally benign form, although not necessarily completely to $CO_2$.

Town gas or manufactured gas plants have contaminated soils with wastes of organic polynuclear aromatic hydrocarbon fused-ring compounds, the higher numbered ring compounds, particularly those having about 4 to about 6 rings, being generally recalcitrant to bioremediation. This recalcitrance is magnified when the contaminant is associated with a solid material, such as soil, and when the organic waste content is high, such as over 5,000 to 10,000 ppm and up to 30,000 to 40,000 ppm, as is the case with many organic polynuclear aromatic hydrocarbon contaminated soils. Solvent extraction of the organic contaminant has been performed to provide a liquid bioremediation system which is known to be more effective than a solid treatment system, but in many instances, the extracting liquids were not compatible with the microorganisms, and the desired uniformity of degradation, particularly of 4- to 6-ring aromatic compounds, could not be obtained.

When referring to 4- to 6-ring polynuclear aromatic hydrocarbon compounds, we mean to include compounds such as pyrene, fluoranthene, chrysene, benz(a)anthracene, benzo(a)pyrene, benzo(e)pyrene, benzo(b)fluoranthene, benzo(k)fluoranthene, benzo(g,h,i)perylene, indeno( 1,2,3-cd)pyrene, dibenzo(a,h)anthracene, and their substituted derivatives. We have found that the hydrogen peroxide chemical oxidation combined with biodigestion according to the present invention preferentially destroys the 4- to 6-fused-ring polynuclear aromatic compounds, as compared to the 2- to 3-fused-ring polynuclear aromatic compounds. The synergism of the integrated chemical/biological treatment process according to the present invention with respect to the 4- to 6-fused-ring polynuclear aromatic hydrocarbon compounds is even further amplified by the concurrent chemical treatment of the contaminated solids with hydrogen peroxide in the presence of a lower alcohol, such as methanol or ethanol. This is especially unexpected because the addition of any organic compound would be expected to quench the oxidation of the polynuclear aromatic hydrocarbon compounds by the hydrogen peroxide, while in this case it significantly increases the oxidation, particularly of 4- to 6-ring polynuclear aromatic hydrocarbon compounds. It is known that the prior addition of organic materials is detrimental; for example, prior composting with cattle manure significantly decreases the desired oxidation effect of hydrogen peroxide because the active hydroxyl ions are apparently consumed by active organic materials other than the polynuclear aromatic hydrocarbon compounds. The lower molecular weight alcohols are thought to increase the aqueous solubility of polynuclear aromatic hydrocarbons, in particular 4- to 6-ring polynuclear aromatic hydrocarbons, thereby rendering them more susceptible to oxidation by Fenton's reaction.

The process for remediation of contaminated solid materials comprising polynuclear aromatic hydrocarbon contaminated solid materials and/or polychlorinated hydrocarbon contaminated materials by sequential biological/chemical/biological treatment in accordance with one embodiment of this invention comprises biodigesting the contaminated solid materials under suitable conditions by a first aerobic or anaerobic digestion, producing a first biodigestion product, contacting for chemical treatment said first biodigestion product with hydrogen peroxide in the presence of ferrous ion in amounts and under conditions suitable for chemical oxidation at a temperature in the range of about 20° C. to 40° C., forming a mixture, and oxidizing said first biodigestion product, producing biodegradable hydrocarbon materials having enhanced biodegradability. In accordance with one particularly preferred embodiment of the process of this invention, the product materials of the chemical treatment are biodigested under suitable conditions by a second aerobic or anaerobic digestion.

In accordance with a particularly preferred embodiment of this invention, the microorganisms for biodigesting said contaminated solid materials and said product materials comprise a microbial culture selected from the group consisting of *Alcaligenes eutrophus*, NRRL No. 15940, Pseudomonas sp. NRRL No. 18064, *Rhodococcus globerulus* $P_6$, ATCC Strain No. 55255 and mixtures thereof. We conducted experiments utilizing *Alcaligenes eutrophus* and Pseudomonas sp. cultures for an extended period of time for mineralization of 2-chlorobiphenyl. The results, as shown in FIG. 1, suggest that both cultures are equally effective in mineralization of 2-chlorobiphenyl with an overall mineralization approaching near 20% on incubation of over 20 days. These experiments were conducted at an optical density for the microorganisms of 1.0 and a pH of 7.0.

Figure 2:
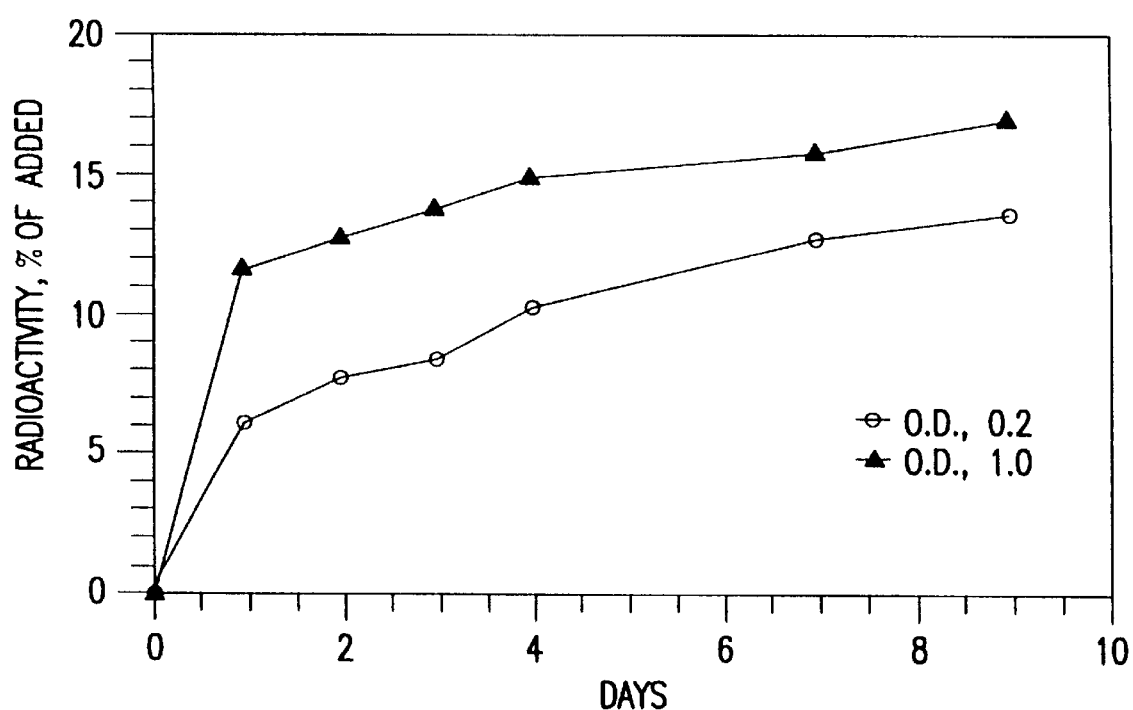
FIG. 2 is a diagram showing the effect of optical density (culture density) on the effectiveness of the process of this invention.
Figure 3:
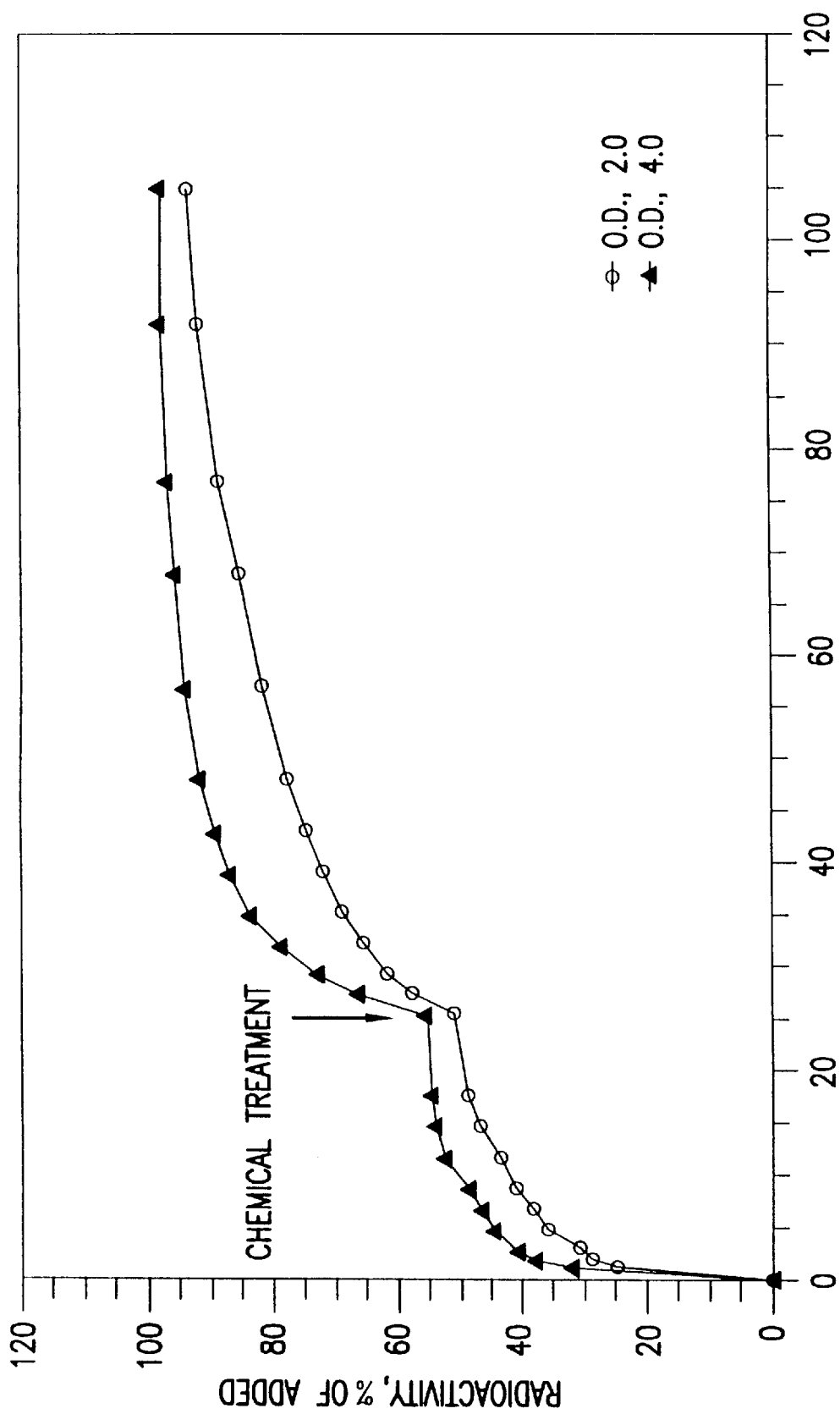
FIG. 3 is a diagram showing the effectiveness of sequential biological-chemical treatment on the mineralization of 2-chlorobiphenyl by resting cells of *Alcaligenes eutrophus* at a pH of 5.0.
Figure 4:
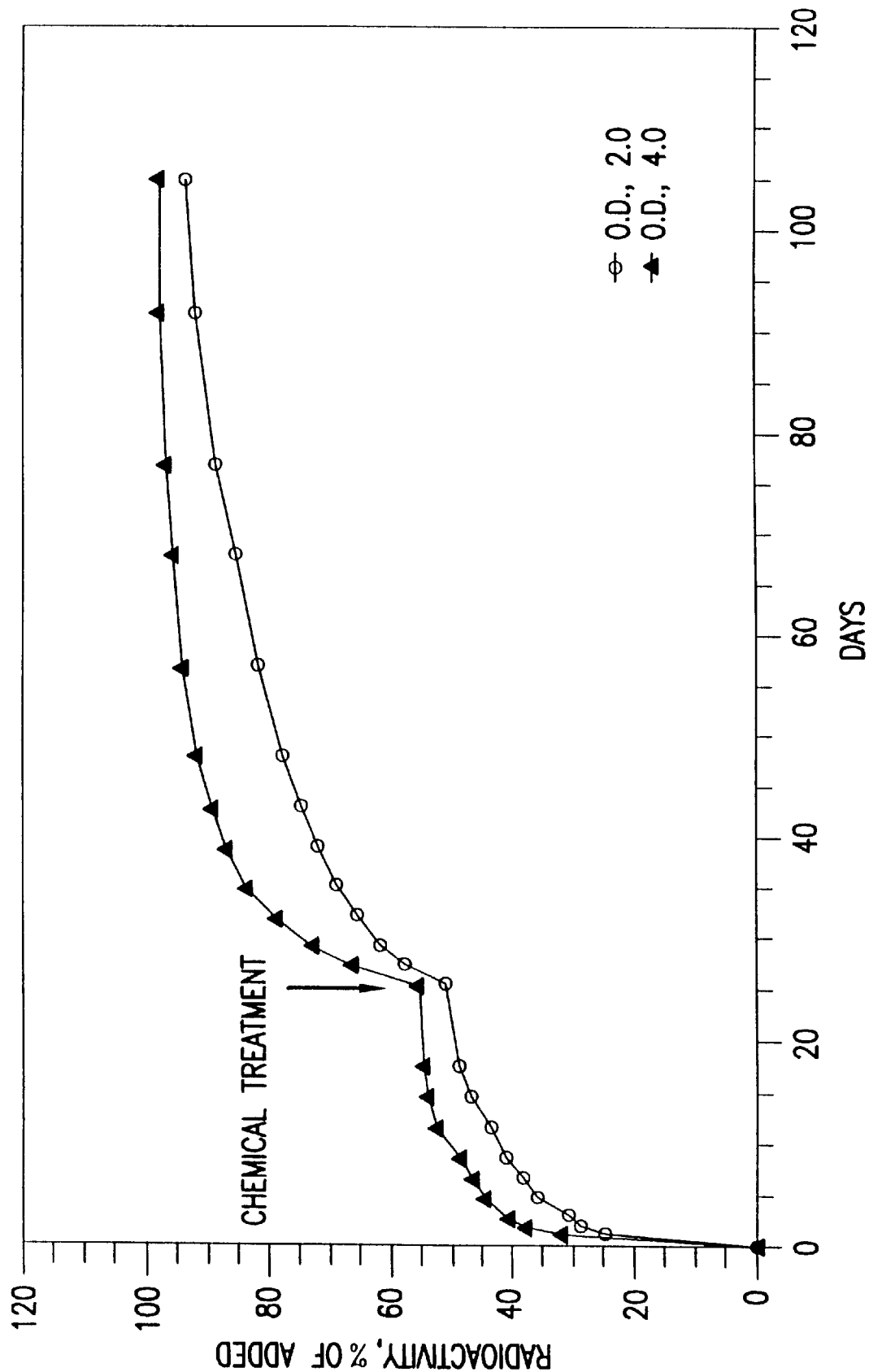
FIG. 4 is a diagram showing the effectiveness of sequential biological-chemical treatment on the mineralization of 2-chlorobiphenyl by resting cells of *Alcaligenes eutrophus* at a pH of 7.0.
Figure 5:
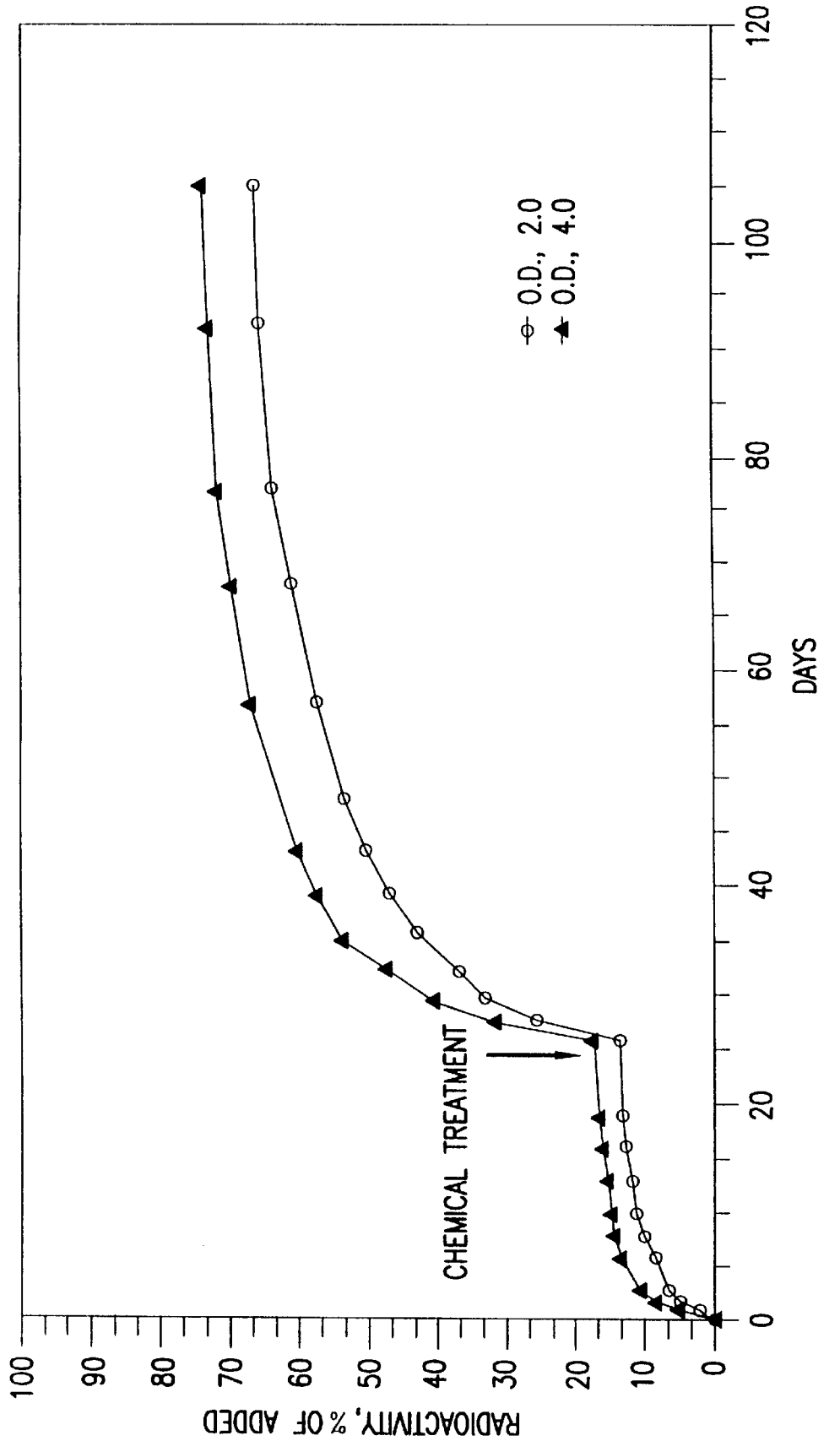
FIG. 5 is a diagram showing the effectiveness of sequential biological-chemical treatment on the mineralization of 2,2',4,4'-tetrachlorobiphenyl by resting cells of *Alcaligenes eutrophus* at a pH of 5.0.
Figure 6:
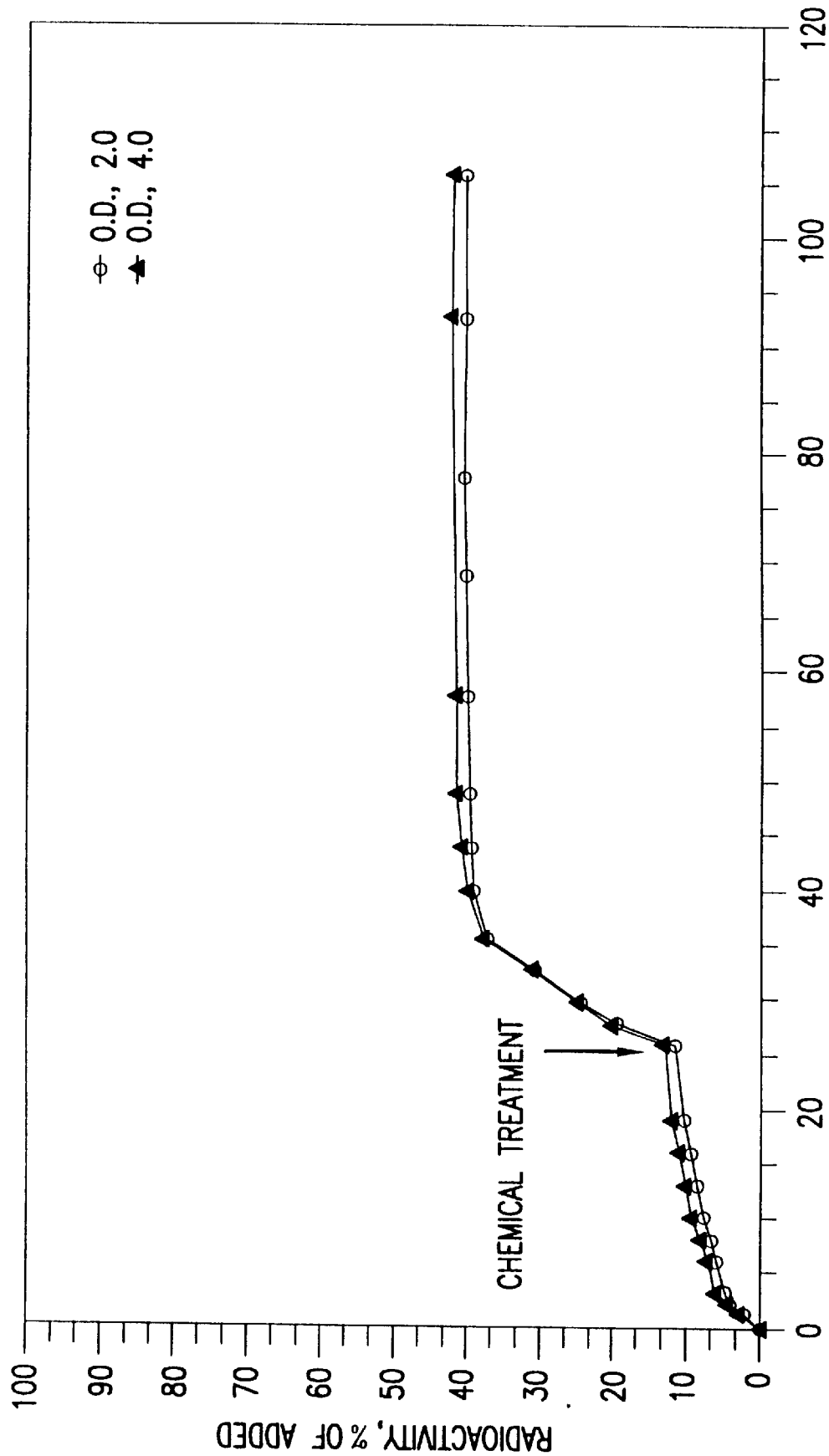
FIG. 6 is a diagram showing the effectiveness of sequential biological-chemical treatment on the mineralization of 2,2',4,4'-tetrachlorobiphenyl by resting cells of *Alcaligenes eutrophus* at a pH of 7.0.
Figure 7:
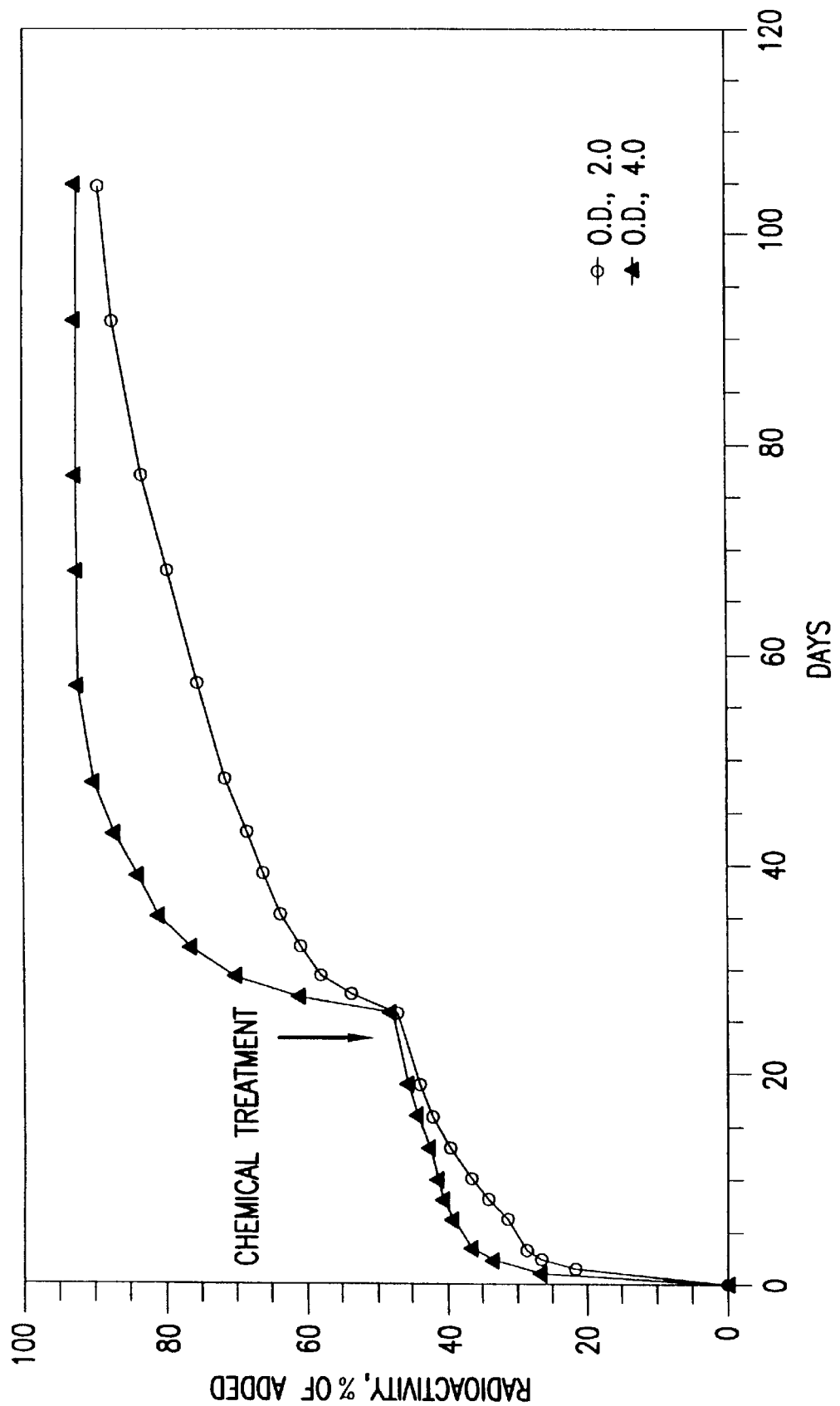
FIG. 7 is a diagram showing the effectiveness of sequential biological-chemical treatment on the mineralization of 2-chlorobiphenyl by resting cells of Pseudomonas sp. at a pH of 5.0.
Figure 8:
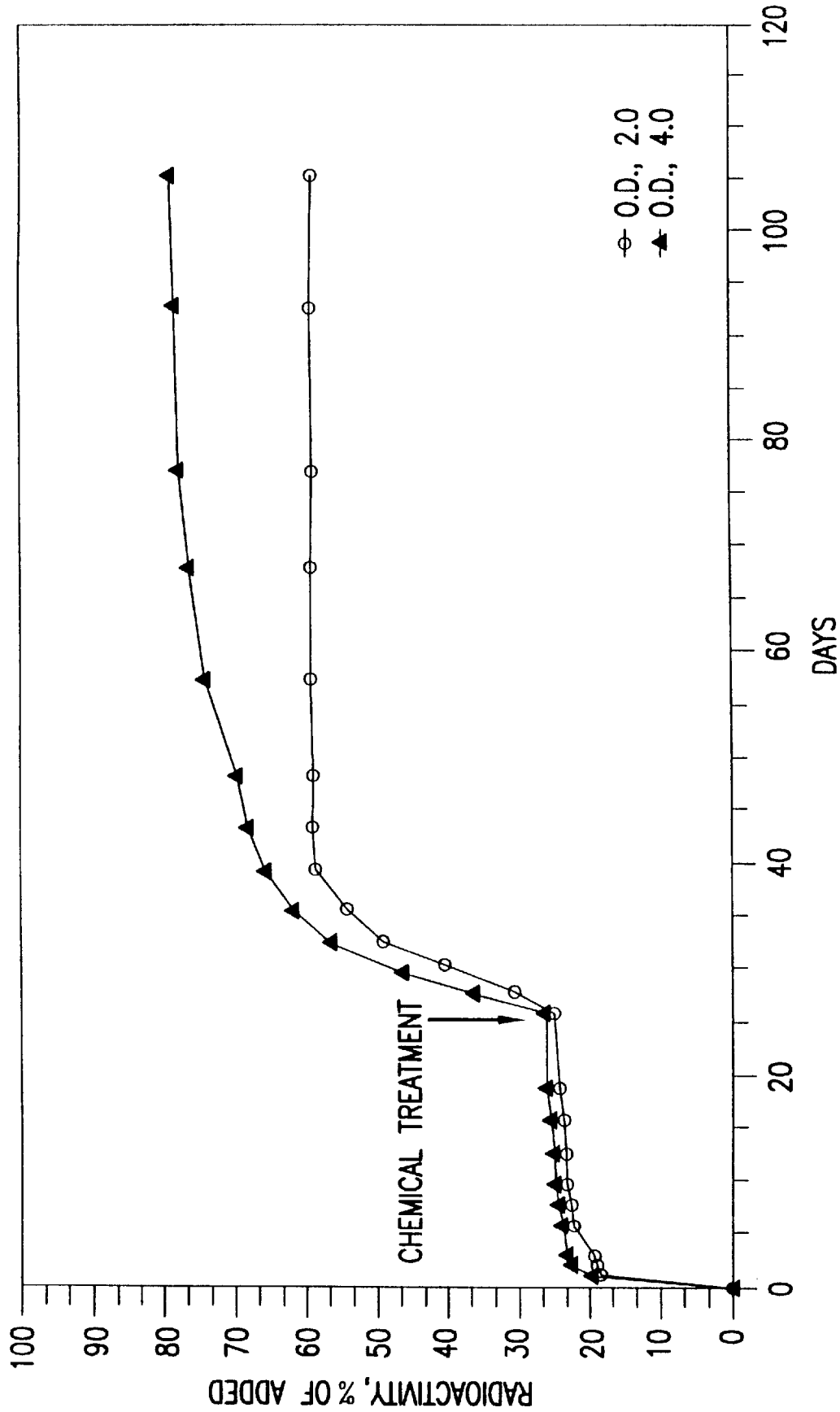
FIG. 8 is a diagram showing the effectiveness of sequential biological-chemical treatment on the mineralization of 2-chlorobiphenyl by resting cells of Pseudomonas sp. at a pH of 7.0.
Figure 9:
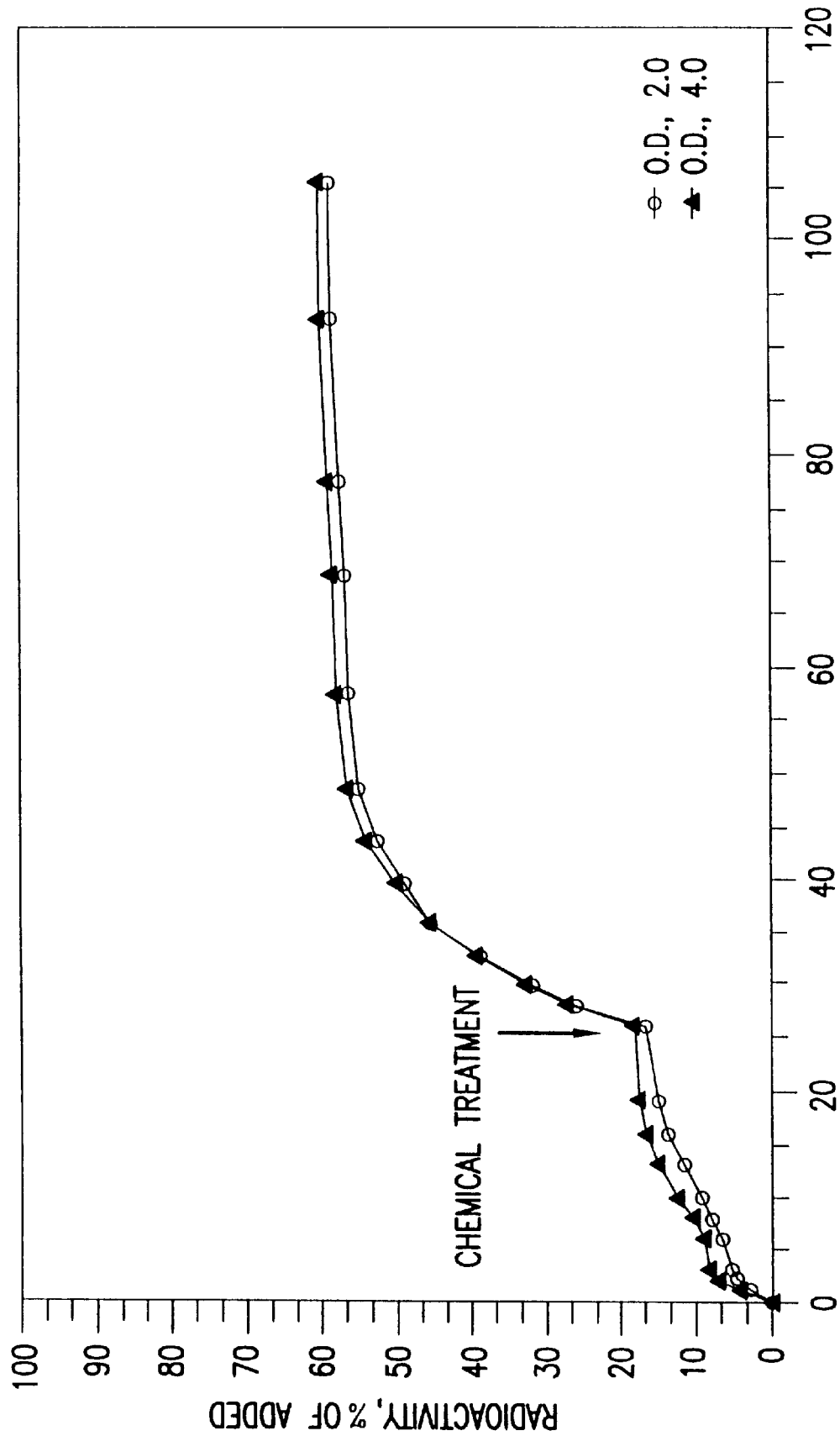
FIG. 9 is a diagram showing the effectiveness of sequential biological-chemical treatment on the mineralization of 2,2',4,4'-tetrachlorobiphenyl by resting cells of Pseudomonas sp. at a pH of 5.0.
Figure 10:
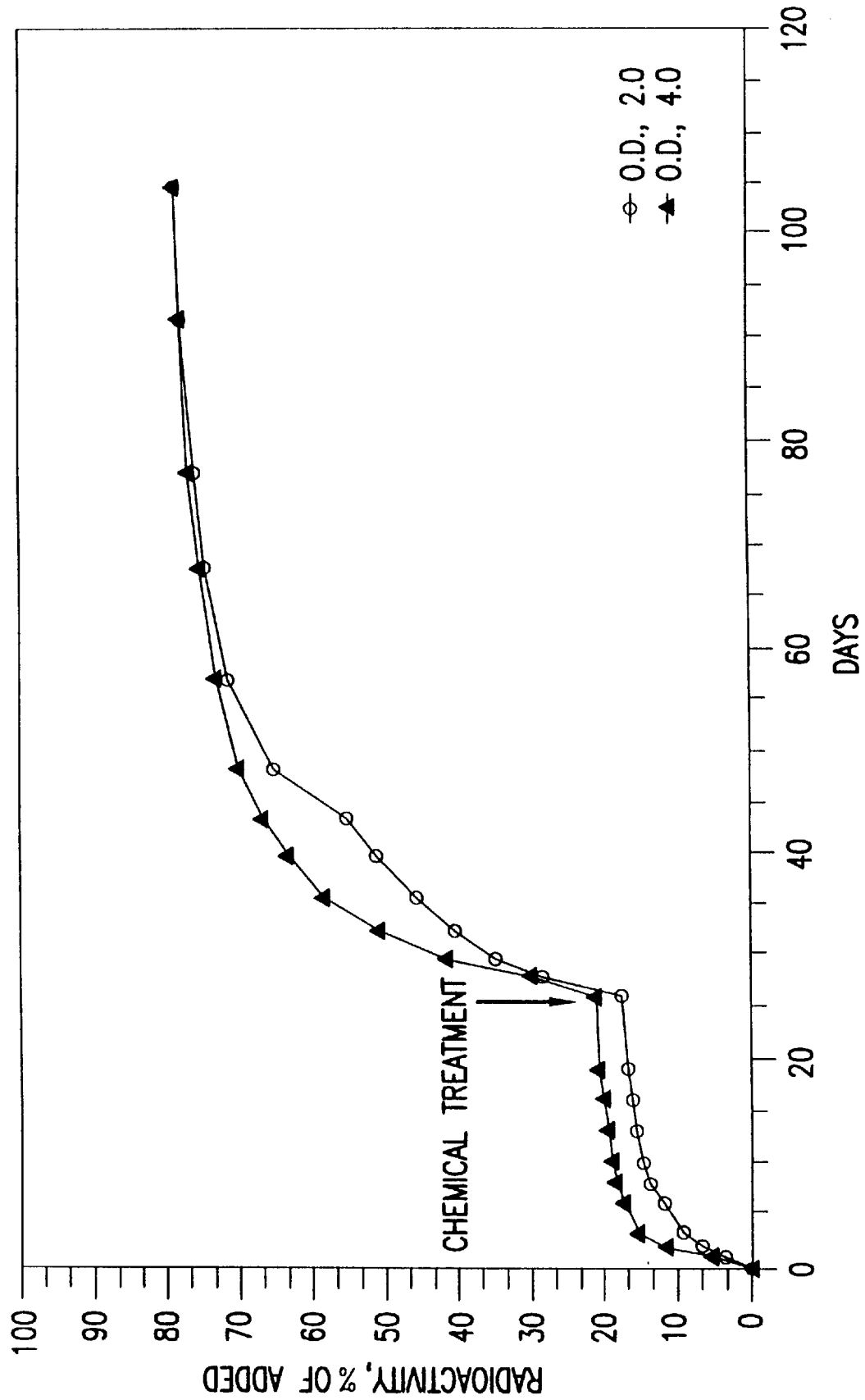
FIG. 10 is a diagram showing the effectiveness of sequential biological-chemical treatment on the mineralization of 2,2',4,4'-tetrachlorobiphenyl by resting cells of Pseudomonas sp. at a pH of 7.0.

FIG. 2 shows the effect of optical density, that is, the concentration of the microorganisms, on the process of this invention. Experiments were conducted with Pseudomonas sp. using two different optical densities (O.D.) of 0.2 and 1.0. The results revealed some enhancement of the mineralization of 2-chlorobiphenyl at an optical density of 1.0 as compared to 0.2. These results suggest that variation of optical density affects the overall mineralization. We have found that mineralization of polychlorinated hydrocarbons in accordance with the process of this invention is greatly enhanced at optical densities greater than 1.0. In accordance with a particularly preferred embodiment of this invention, the optical density of the media comprising the microorganisms is in the range of about 2.0 to 4.0.

FIGS. 3–6 show the effect of pH on the mineralization of PCBs in accordance with the process of this invention. Studies were conducted in which PCBs were subjected to biological treatment with *Alcaligenes eutrophus* for 26 days followed by treatment with Fenton's Reagent (4% $H_2O_2$). Optical densities of 2.0 and 4.0 were evaluated at pHs of 5.0 and 7.0 for *Alcaligenes eutrophus*. The results for mineralization of 2-chlorobiphenyl and 2,2',4,4'-tetrachlorobiphenyl are shown in FIGS. 3–6. Mineralization in excess of 98% was achieved for 2-chlorobiphenyl using *Alcaligenes eutrophus* at a pH of 5.0 and an optical density of 4.0. However, even at an optical density of 2.0, mineralization of 94% was achieved, suggesting that a pH of 5.0, as compared to pH's in the range of 7.0 to 7.5 as are typically employed with *Alcaligenes eutrophus*, is very effective for biological mineralization of 2-chlorobiphenyl using *Alcaligenes eutrophus*.

A comparative study undertaken at a pH of 7.0 showed that biological mineralization of 82% and 71% was achieved at optical densities of 4.0 and 2.0, respectively, using *Alcaligenes eutrophus*. These results clearly demonstrate that a pH of 5.0, which is substantially below the pH normally employed with *Alcaligenes eutrophus*, is more effective for mineralization of 2-chlorobiphenyl than a pH of 7.0. Mineralization of over 56% was achieved with biological treatment alone in less than 26 days. After chemical treatment with Fenton's Reagent in accordance with the process of this invention, a total mineralization of 98% was achieved within 106 days.

Experiments conducted with 2,2',4,4'-tetrachlorobiphenyl at pHs of 5.0 and 7.0 and optical densities of 2.0 and 4.0 showed similar results. Mineralization of 74% and 82% of the 2,2',4,4'-tetrachlorobiphenyl was achieved at a pH of 5.0 and optical densities of 2.0 and 4.0, respectively. By comparison, mineralization of only 44% and 50% was achieved at a pH of 7.0 and optical densities of 2.0 and 4.0, respectively.

FIGS. 7–10 show the results of application of the process of this invention to Pseudomonas sp. As can be seen, mineralization of more than 95% of the PCBs was achieved at an optical density of 4.0 and a pH of 5.0. The overall pattern with Pseudomonas sp. was similar to the results obtained with *Alcaligenes eutrophus*. Thus, it is clear from these results that a pH of 5.0 is more suitable for achieving complete mineralization of 2-chlorobiphenyl using either *Alcaligenes eutrophus* or Pseudomonas sp. followed by chemical treatment in accordance with the process of this invention. Operation of the process of this invention at a pH of 5.0 resulted in more than a 90% mineralization of PCBs. Accordingly, it is preferred that the process of this invention be carried out at a pH less than 7.0, preferably in the range of about 4.0 to 6.0.

*Alcaligenes eutrophus* or Pseudomonas sp. are equally effective in the biological treatment of 2-chlorobiphenyl in accordance with the process of this invention resulting in over 50% mineralization in 26 days. However, when applied to 2,2',4,4'-tetrachlorobiphenyl, biological treatment resulted in mineralization of only about 23% in 26 days. Chemical treatment using Fenton's Reagent enhanced mineralization rates in that mineralization of about 75% was achieved in a total time less than 106 days with a final degradation value of 82% being obtained at 106 days.

The effects of biological, chemical and various combinations of these treatments were examined at several different time intervals from 4 to 21 days. The results show that almost 50% of the PCBs could be degraded within 4 days using biological treatment (Table 1). However, untreated soil did not show significant degradation, revealing that bioaugmentation was necessary for improvement of overall degradation. At a pH of 7.0, treatment of the slurry with a mixed culture of Pseudomonas sp. and *Alcaligenes eutrophus* was more effective as compared to chemical treatment at the same pH. A combination of biological followed by chemical treatment was slightly better as compared to biological treatment alone. A subsequent biological treatment showed a further enhancement in PCB degradation with over 70% PCBs degraded within 15 days. This demonstrates further that chemical treatment alters the overall composition of PCBs in such a way that it enhances the accessibility by biodegradation.

TABLE 1

EFFECT OF CHEMICAL AND BIOLOGICAL TREATMENT OF PCBs IN SOIL SLURRY (pH 7,O)

| Treatment | PCB, ppm |
| --- | --- |
| Initial Concentration | 275.0 |
| Untreated | 207.0 |
| Chemical Only | 194.5 |
| Biological Only | 110.0 |
| Biological + Chemical | 100.0 |
| Biological + Chemical + Biological | 60.0 |

The chemical treatment portion of the process according to the present invention is carried out by contacting for chemical treatment polynuclear aromatic hydrocarbon contaminated solid material or polychlorinated hydrocarbon contaminated material, after having first been aerobically or anaerobically biodigested, with a liquid solution, preferably aqueous, forming a mixture containing at least sufficient, and preferably an excess of, ferrous ion to enable complete reaction with the total added hydrogen peroxide to form the desired hydroxyl radical oxidant. We have found amounts, based upon the total mixture being treated, of about 0.1 weight percent to about 10 weight percent total hydrogen peroxide and about 0.1 to about 1% by weight $FeSO_4$ to be effective. Preferred amounts of hydrogen peroxide are about 0.5 to about 5.0 weight percent, based upon the total mixture being treated. We have found that as low as 5.0 weight percent hydrogen peroxide preferentially removes in excess of 70 percent of the polynuclear aromatic hydrocarbon compounds having 4 to 6 rings. The amount of hydrogen peroxide may also be expressed as about 10 mg to about 0.5 gram per gram of solids, such as soil in a slurry, to be treated. The solid/liquid contacting may be best achieved by suspending the solids in a liquid slurry. We have found that the chemical treatment portion of the process functions well at comparatively high solids concentrations of about 10 to about 90 weight percent solids, based upon the total slurry. It is preferred that agitation of the slurry be maintained for about 1 to about 12 hours following completion of hydrogen peroxide addition. The pH of the slurry being treated should be acidic and preferably a pH of about 4.0 to about 6.0 is suitable.

The chemical treatment portion of the sequential biological/chemical/biological treatment process of this invention is carried out at about 10° C. to about 100° C. We have found a significant decrease in desired oxidation of polynuclear aromatic hydrocarbon compounds at both lower and higher temperatures. We prefer to carry out the chemical treatment portion of the process of this invention at temperatures about 20° C. to about 40° C. In preferred embodiments, due to the exothermic nature of the chemical reactions, the temperature is maintained by slow addition of hydrogen peroxide to the slurry solution containing at least sufficient ferrous ion to react with all of the hydrogen peroxide to be added. The ferrous ion may be provided in an aqueous solution by hydrated $FeSO_4$ or any other iron salt or source which will provide the ferrous ion in the liquid solution. We have found suitable rates of addition of hydrogen peroxide to the liquid solution to maintain desired temperatures are between about 1 milligram to about 300 milligrams hydrogen peroxide per hour per gram of contaminated solid material, dependent upon the material being treated, and preferably about 1 to about 100 milligrams hydrogen peroxide per hour per gram contaminated solid material.

The chemical treatment portion of the process of this invention produces primarily carbon dioxide and water, which are environmentally acceptable, and, to a much lesser extent, partially oxidized products of polynuclear aromatic hydrocarbon compounds, such as hydroxylated or epoxidated compounds, and polychlorinated hydrocarbon compounds which are much more susceptible to bioremediation than the original polynuclear aromatic hydrocarbons, particularly those containing 4 to 6 rings or the original polychlorinated hydrocarbons. In work we have completed, a complex 5-ring compound, benzo(a)pyrene, was labeled with radioactive carbon and our tests showed that up to about 40% of the labeled carbon was collected as $CO_2$ following a single chemical treatment in accordance with the present invention. This represents total oxidation of a substantial portion of the biorecalcitrant material.

In accordance with one embodiment of the process of this invention, in the chemical treatment portion of the integrated process of this invention, a lower alcohol, such as methanol or ethanol or mixtures thereof, is added to the liquid solution. Such addition of a lower alcohol is particularly preferred where large numbers of weathered 4- to 6-ring polynuclear aromatic hydrocarbons are present. Suitable amounts of alcohol are about 0.1 to about 80 volume percent, based on the total slurry and preferably about 1 to about 10 volume percent. The alcohol is miscible in water of the slurry and is not harmful to the later biodigestion process. The presence of alcohol in the slurry results in unexpectedly high and frequently complete oxidation of the polynuclear aromatic hydrocarbons, particularly those with 4 to 6 carbon atoms. This result is unexpected to us because it would be expected that addition of any organic material would quench the activity of the hydrogen peroxide upon the polynuclear aromatic hydrocarbons. For example, we have found inhibition of complete oxidation of benzo(a)pyrene in an amount of about 70 percent inhibition when 10 weight/volume percent glucose or cellulose or lignin is added to the slurry in a similar manner.

Figure 11:
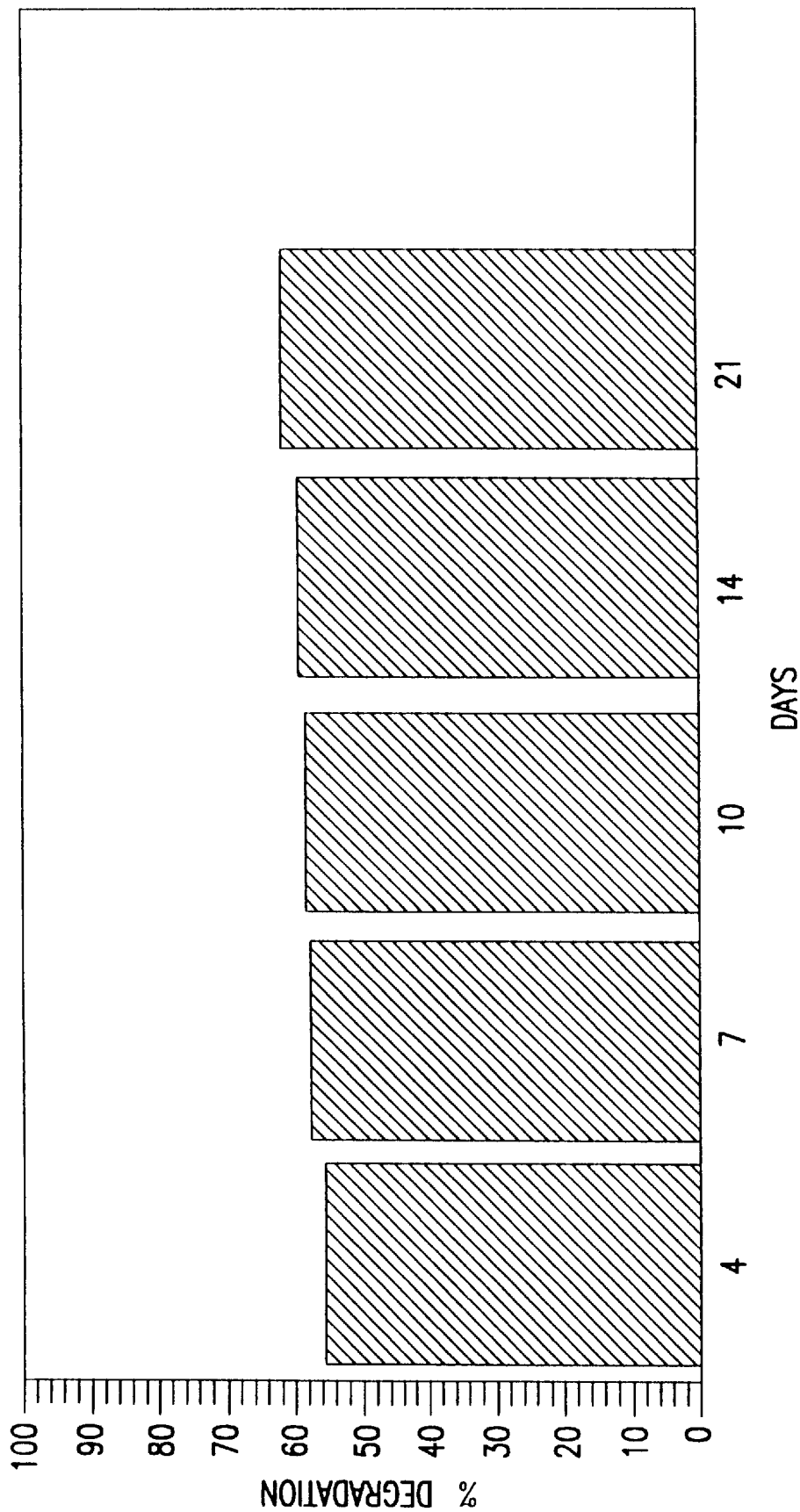
FIG. 11 is a diagram showing the effect of different incubation times on PCB degradation by biological treatment in accordance with this invention.
Figure 12:
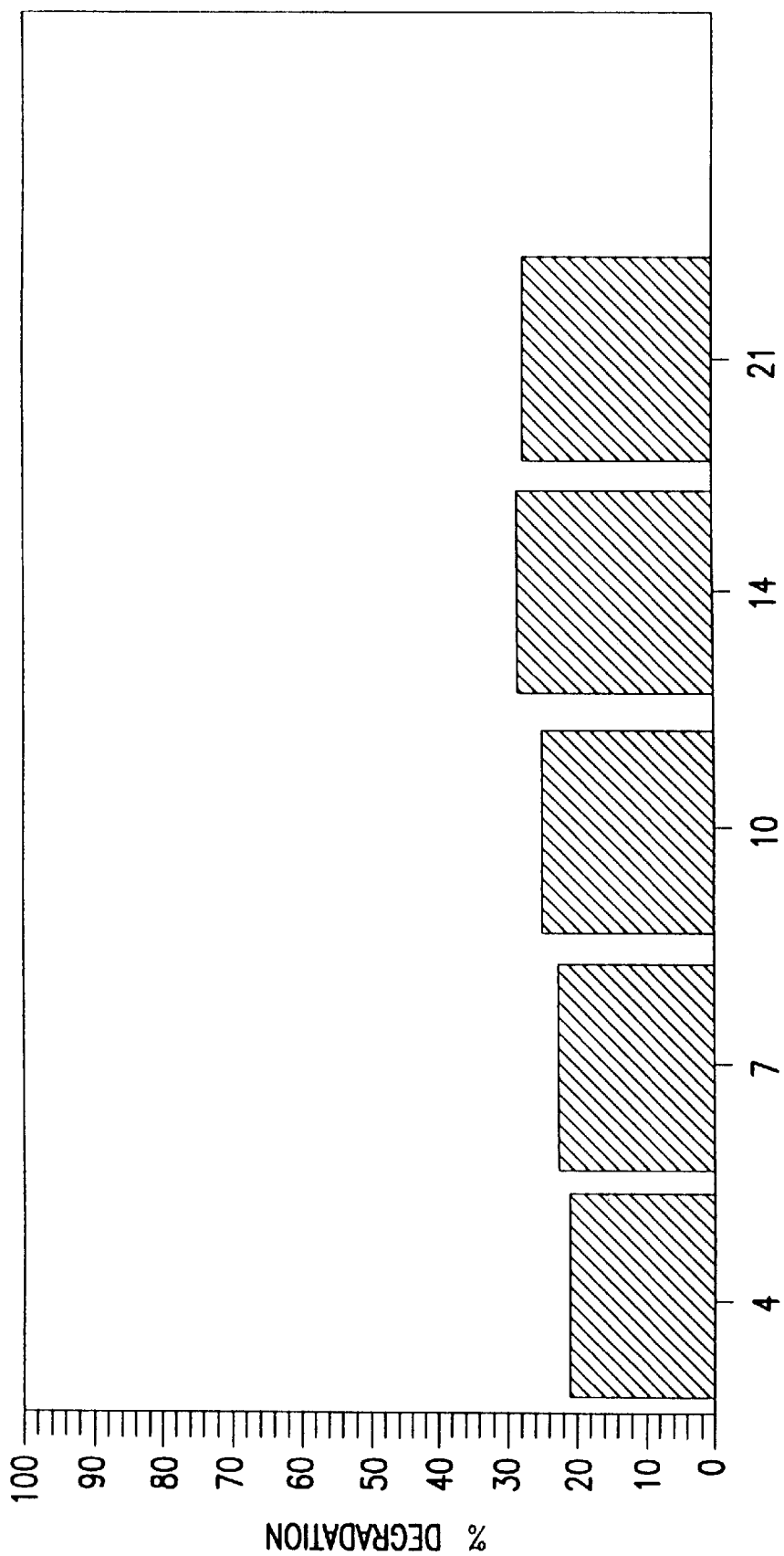
FIG. 12 is a diagram showing the effect of different incubation times on PCB degradation by chemical treatment.
Figure 13:
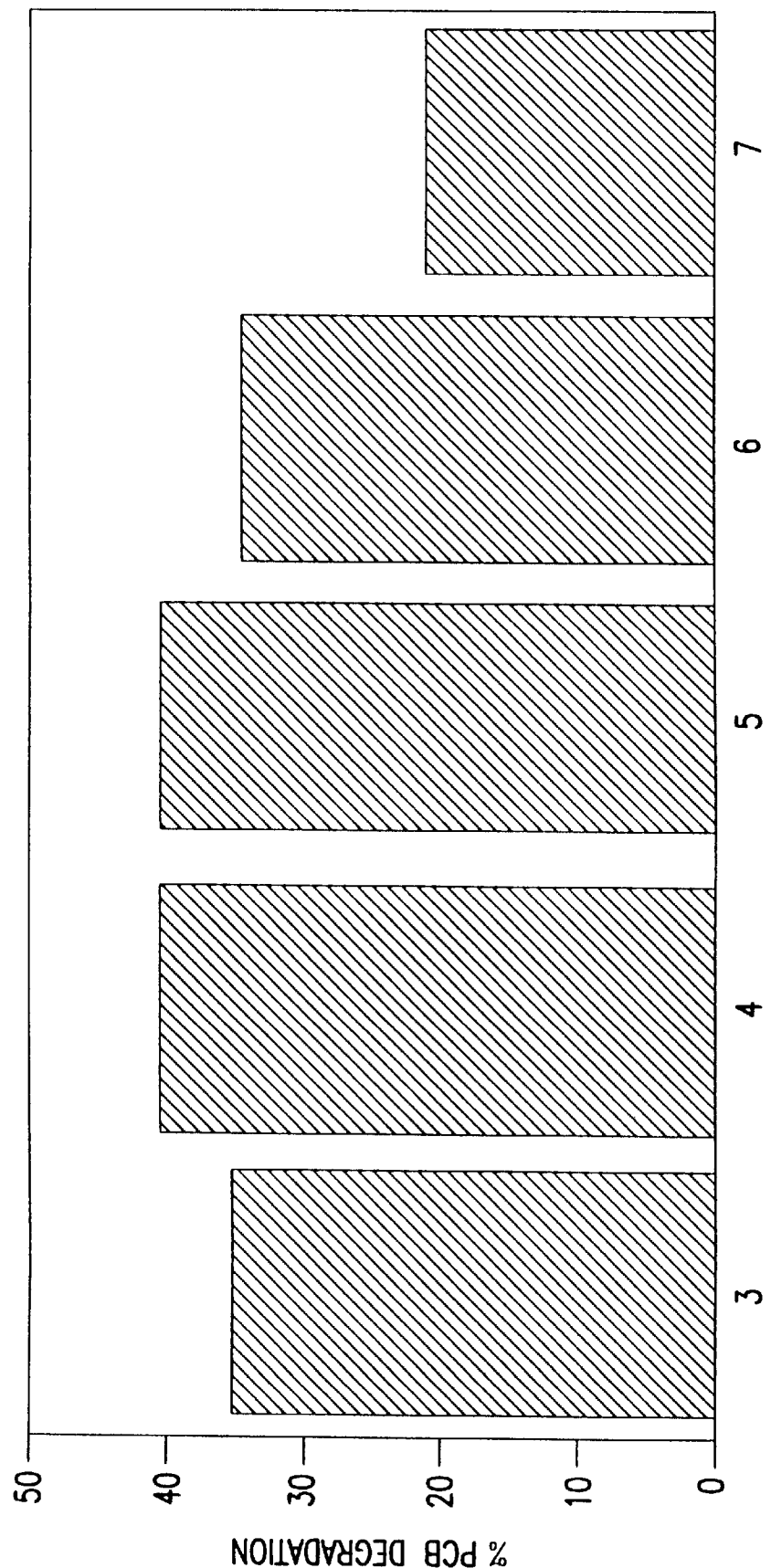
FIG. 13 is a diagram showing the effect of pH on Fenton's Reagent treatment of soil slurry in bench scale studies.
Figure 14:
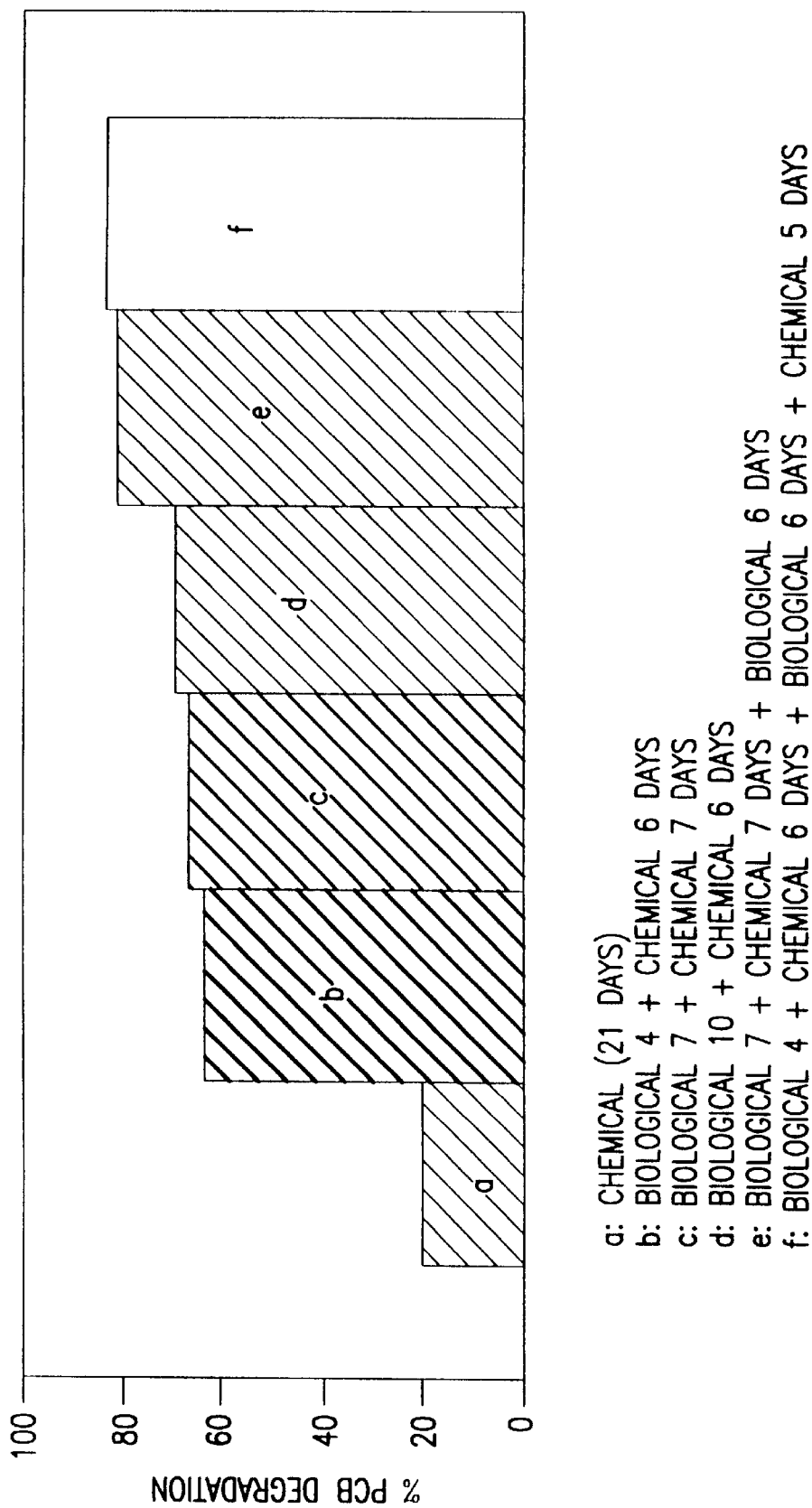
FIG. 14 is a diagram showing the results of PCB degradation using various embodiments of the process of this invention compared to sequential biological-chemical treatment.

Optimization studies were conducted by determining the performance of biological treatment and chemical treatment of soil at different time intervals at a pH 7. The results are shown in FIGS. 11 and 12. In summary, the results indicate that 56% degradation of PCB, using biological treatment, was obtained within 4 days with the degradation increasing slightly to 66% after 21 days incubation. The chemical treatment was not very effective as only 21% degradation of PCB was achieved in 4 days of batch incubation with a maximum of 29% after 14 days of incubation. The chemical treatment was further examined at several different pHs, the results of which are shown in FIG. 13. These results show that over 41% degradation of the PCBs was obtained at pHs of 4.0 and 5.0 while only 21% degradation was obtained at a pH of 7.0. At a pH of 5.0 for biological treatment, over 83% of PCB degradation by the integrated biological/chemical/biological approach in accordance with the process of this invention was obtained (FIG. 14). These results demonstrate that a pH of 5.0. is suitable for PCB degradation.

Figure 15:
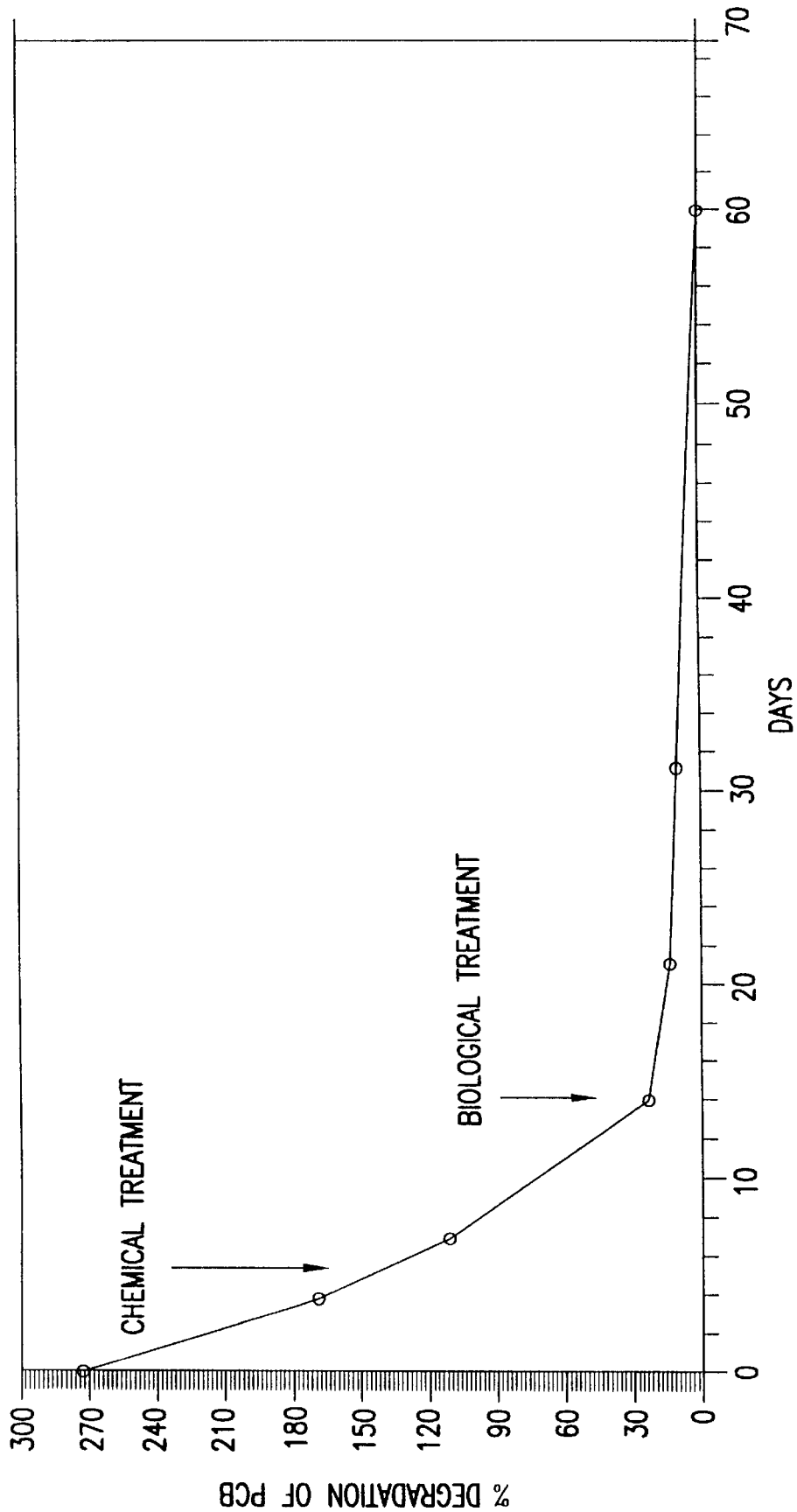
FIG. 15 is a diagram showing the results of a bench scale treatment of actual soil in accordance with the process of this invention.

Large reactor studies were conducted for degradation of PCBs in an agitated and aerated vessel. Experiments were carried out in a 7 liter reactor with an initial volume of 2.5 L and 20% slurry. The objective was to compare the PCB degradation pattern to vial study results. The slurry was continuously aerated at low level by sparging of air (20 ml/min). A pH of 5.0 was employed in this work and an optical density of 2.0 was utilized for bioslurry preparation. The treatment was continued with the bioslurry consisting of mixed cultures of Alcaligenes eutrophus and Pseudomonas sp. for 4 days. The reactor pH was continuous monitored using a data acquisition system. The pH increased from 5.17 to 5.61 in 4 days, evidencing degradation of PCBs by the bioslurry. Subsequently, Fenton's Reagent (2% $H_2O_2$) was added to the bioslurry mixture. Addition of Fenton's Reagent resulted in a slight drop in pH to 5.47, which was further reduced to 5.2 by addition of dilute HCl. The chemical treatment was continued for another 3 days. The pH increased up to 5.72, again evidencing the degradation of PCBs. The results, summarized in FIG. 15, show that PCBs in the contaminated soils were completely degraded in 2 months treatment with more than 99% degradation occurring within a month after biological/chemical/biological treatment in accordance with the process of this invention.

Figure 16:
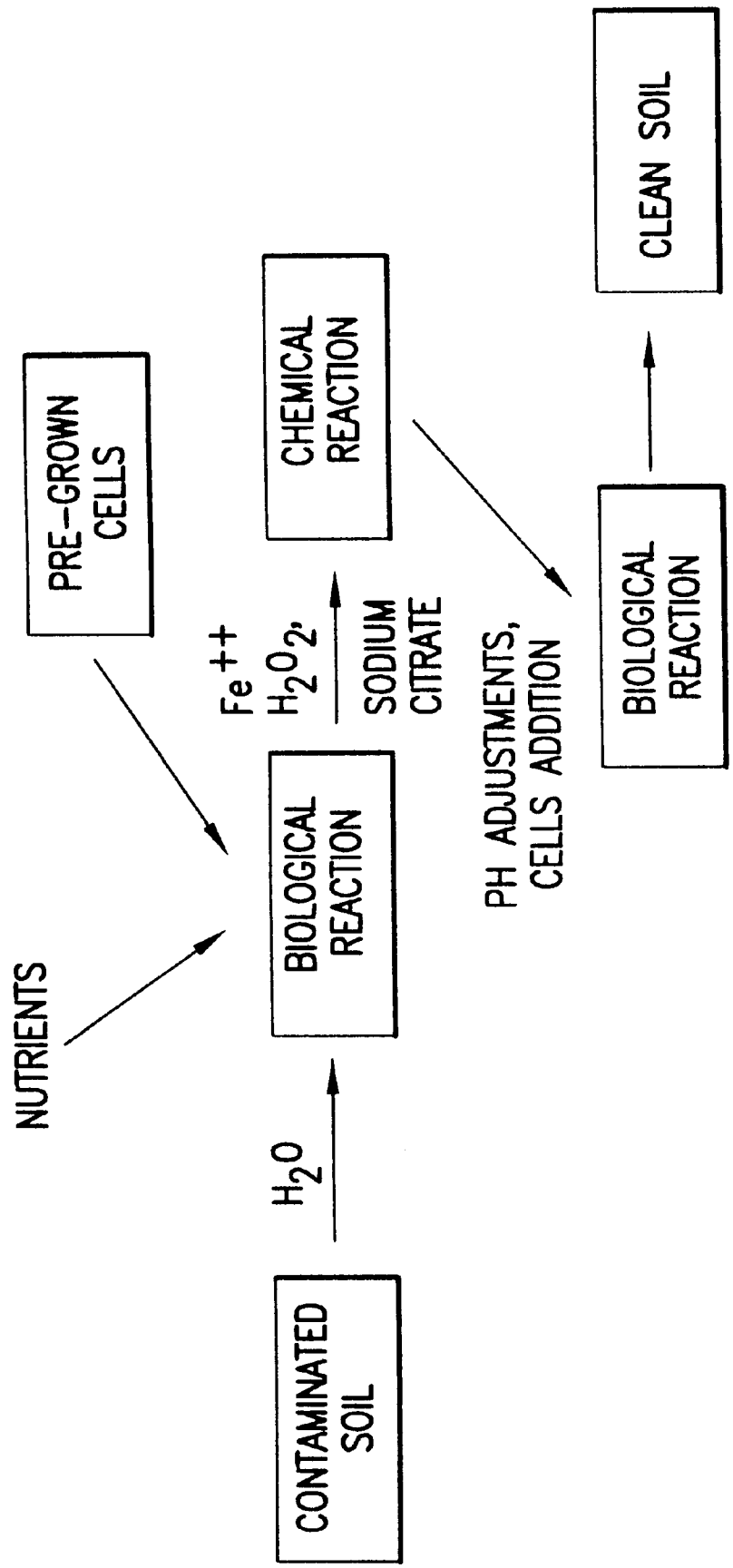
FIG. 16 is a process flow diagram for degradation of polychlorinated hydrocarbons by the sequential biological-chemical-biological treatment process of this invention.

FIG. 16 is a schematic diagram of the process of this invention. Cells of microorganisms suitable for use in the process of this invention were grown aerobically at 30° C. in a gyratory shaker. The medium was a phosphate buffered mineral salts medium (PAS) containing biphenyl as a carbon source and supplemented with 0.005% yeast extract. PAS medium was prepared by adding 77.5 ml of PA concentrate comprising $K_2HPO_4$ (56.77 g/l), $KH_2PO_4$ (21.94 g/liter), and $NH_4Cl$ (27.61 g/liter), and 50 mg of yeast extract to 910 ml of glass-distilled water. After autoclaving and upon cooling, 10 of sterile PAS 100× salts comprising $MgSO_4$ (19.5 g/liter), $MnSO_4 \cdot H_2O$ (5 g/liter), $FeSO_4 \cdot 7H_2O$ (1 g/liter), and $CaCl_2 \cdot 2H_2O$ (0.3 g/liter) along with several drops of concentrated $H_2SO_4$ per liter to prevent precipitation of basic salts, was added. Commercially available biphenyl was then added. Growth of the cells in the PAS medium was carried out for a period of 24 to 48 hours, after which the cells were harvested and suspended in phosphate buffer. Thereafter, the cells are mixed with the PCB congeners and incubated (biodigested) for a period of 2 to 4 weeks. The resulting mixture is then chemically treated by contact with Fenton's reagent ($H_2O_2$ 4% v/v; $FeSO_4$ 10 mM) followed by further biodigestion for a period of 4 to 8 weeks.

While in the foregoing specification this invention has been described in relation to certain preferred embodiments thereof, and many details have been set forth for the purpose of illustration, it will be apparent to those skilled in the art that the invention is susceptible to additional embodiments and that certain of the details described herein can be varied considerably without departing from the basic principles of the invention.

We claim:

1. A process for remediation of contaminated solid materials selected from the group consisting of polynuclear aromatic hydrocarbon contaminated solid materials, polychlorinated hydrocarbon contaminated materials, and mixtures thereof by sequential biological/chemical/biological treatment comprising the steps of:

biodigesting said contaminated solid materials under suitable conditions by a first aerobic or anaerobic digestion, producing a first biodigestion product;

contacting for chemical treatment said first biodigestion product with hydrogen peroxide in the presence of ferrous ion in amounts and under conditions suitable for chemical oxidation at a temperature in the range of about 10° C. to 100° C., forming a mixture, and oxidizing said first biodigestion product, producing biodegradable hydrocarbon materials having enhanced biodegradability; and biodigesting under suitable conditions said product materials by one of a second aerobic or anaerobic digestion.

2. A process in accordance with claim 1, wherein a microorganism for biodigesting said contaminated solid materials and said product materials comprises a microbial culture selected from the group consisting of *Alcaligenes eutrophus,* Pseudomonas sp., Rhodococcus and mixtures thereof.

3. A process in accordance with claim 1, wherein said first aerobic or anaerobic digestion is carried out at a pH in the range of about 4.0 to 6.0.

4. A process in accordance with claim 2, wherein said microorganism is concentrated to an optical density in the range of about 0.2 to 5.0.

5. A process in accordance with claim 1, wherein the total of said hydrogen peroxide is about 0.1 to about 10 weight percent of said mixture.

6. A process in accordance with claim 1, wherein the total of said hydrogen peroxide is about 0.5 to about 5 weight percent of said mixture.

7. A process in accordance with claim 1, wherein said hydrogen peroxide is added at a rate sufficient to maintain said temperature.

8. A process in accordance with claim 7, wherein said hydrogen peroxide is added at a rate of about 1 milligram to about 300 milligrams hydrogen peroxide per hour per gram of said contaminated solid materials.

9. A process in accordance with claim 7, wherein said hydrogen peroxide is added at a rate of about 1 milligram to about 100 milligrams hydrogen peroxide per hour per gram of said contaminated solid materials.

10. A process in accordance with claim 1, wherein said contaminated solid materials comprise at least one of soil and sediment.

11. A process in accordance with claim 1, wherein said contaminated solid materials comprise about 10 to about 90 weight percent of said mixture.

12. A process in accordance with claim 1, wherein said hydrogen peroxide and said ferrous ion are disposed in a liquid solution comprising a lower alcohol.

13. A process in accordance with claim 12, wherein said lower alcohol is selected from the group consisting of methanol, ethanol and mixtures thereof.

14. A process in accordance with claim 12, wherein said lower alcohol is present in an amount of about 0.1 to about 80 volume percent, based upon the volume of said mixture.

15. A process in accordance with claim 12, wherein said lower alcohol is present in an amount of about 1 to about 10 volume percent, based upon the total mixture.

16. A process in accordance with claim 1, wherein a predominate portion of said polynuclear aromatic hydrocarbon comprises 4 to 6 carbon rings.

17. A process in accordance with claim 1, wherein said polynuclear aromatic hydrocarbon comprise predominately 4 to 6 carbon rings, the total of said hydrogen peroxide is about 0.1 to about 10 weight percent of said contaminated solid materials and said mixture, and said hydrogen peroxide is added at a rate sufficient to maintain said temperature.

18. A process for in-situ remediation of contaminated soil particles selected from the group consisting of polynuclear aromatic hydrocarbon contaminated soil particles, polychlorinated hydrocarbon contaminated soil particles, and mixtures thereof by sequential biological/chemical/biological in-situ treatment comprising the steps of:

biodigesting said contaminated soil particles under suitable conditions by a first aerobic or anaerobic digestion, producing a first biodigestion product;

contacting for chemical treatment said first biodigestion product with hydrogen peroxide in the presence of ferrous ion in amounts and under conditions suitable for chemical oxidation at a temperature of about 20° C. to about 100° C., oxidizing said contaminants producing biodegradable hydrocarbon product materials having enhanced biodegradability, and biodigesting under suitable conditions said product materials by a second aerobic or anaerobic biodigestion.

19. A process in accordance with claim 18, wherein said hydrogen peroxide and said ferrous ion are disposed in a liquid solution comprising a lower alcohol.

20. A process in accordance with claim 19, wherein said lower alcohol is present in an amount of about 0.1 to about 80 volume percent, based upon said solid materials and said liquid.

* * * * *